(12) United States Patent
Wong et al.

(10) Patent No.: US 9,506,934 B2
(45) Date of Patent: Nov. 29, 2016

(54) POLYMER TEST CARTRIDGE MIXER FOR CELL LYSIS

(71) Applicant: Honeywell International Inc., Morristown, NJ (US)

(72) Inventors: Pamela Wong, White Bear Lake, MN (US); Phillip Henning, Minneapolis, MN (US); Elizabeth Palaima, St. Paul, MN (US)

(73) Assignee: Honeywell International Inc., Morris Plains, NJ (US)

( * ) Notice: Subject to any disclaimer, the term of this patent is extended or adjusted under 35 U.S.C. 154(b) by 160 days.

(21) Appl. No.: 13/872,977

(22) Filed: Apr. 29, 2013

(65) Prior Publication Data

US 2014/0322697 A1    Oct. 30, 2014

(51) Int. Cl.
*G01N 33/72* (2006.01)
*B01F 13/00* (2006.01)
*B01L 3/00* (2006.01)
*B01F 5/06* (2006.01)

(52) U.S. Cl.
CPC ........... *G01N 33/726* (2013.01); *B01F 5/0641* (2013.01); *B01F 13/0059* (2013.01); *B01L 3/502746* (2013.01); *B01L 2200/10* (2013.01); *B01L 2300/0816* (2013.01); *B01L 2300/0874* (2013.01); *B01L 2300/0883* (2013.01); *B01L 2300/0887* (2013.01)

(58) Field of Classification Search
CPC ................... B01L 2300/816; B01L 2300/088; B01L 2300/0887; B01L 2200/16; G01N 33/726; B01F 13/0059; B01F 13/0061; B01F 13/009

USPC ........ 422/502–503, 554, 402, 408, 420–421, 422/425–426
See application file for complete search history.

(56) References Cited

U.S. PATENT DOCUMENTS

| | | | |
|---|---|---|---|
| 6,321,791 B1 * | 11/2001 | Chow | 137/833 |
| 6,536,477 B1 * | 3/2003 | O'Connor et al. | 137/833 |
| 6,537,501 B1 * | 3/2003 | Holl et al. | 422/537 |
| 6,676,835 B2 * | 1/2004 | O'Connor et al. | 210/542 |
| 6,748,978 B2 * | 6/2004 | Pezzuto et al. | 137/833 |
| 6,845,787 B2 * | 1/2005 | Karp et al. | 137/833 |
| 6,890,093 B2 * | 5/2005 | Karp et al. | 366/336 |
| 7,077,152 B2 * | 7/2006 | Karp | 137/15.18 |

(Continued)

FOREIGN PATENT DOCUMENTS

| | | |
|---|---|---|
| EP | 1123734 A2 | 8/2001 |
| WO | WO-99/60397 A1 | 11/1999 |
| WO | WO-2008/084245 A2 | 7/2008 |
| WO | WO-2010/114858 A1 | 10/2010 |

OTHER PUBLICATIONS

"European Application Serial No. 14164516.8, European Search Report mailed Sep. 1, 2014", 8 pgs.

(Continued)

*Primary Examiner* — Brian R Gordon
(74) *Attorney, Agent, or Firm* — Schwegman Lundberg & Woessner, P.A.

(57) ABSTRACT

A multiple polymer layer test cartridge includes an input to receive a sample containing cells, multiple lysing channel structures on alternate layers of the multiple layer test cartridge coupled to each other to pass the sample in sequence between the lysing channel structures, and a test chamber to receive the sample from the multiple lysing channel structures.

13 Claims, 3 Drawing Sheets

(56) References Cited

U.S. PATENT DOCUMENTS

| | | | |
|---|---|---|---|
| 7,632,470 B2* | 12/2009 | Tabata et al. | 422/130 |
| 7,708,950 B2* | 5/2010 | Yamada et al. | 422/504 |
| 8,058,072 B2* | 11/2011 | Seki et al. | 436/43 |
| 2002/0185184 A1 | 12/2002 | O'Connor et al. | |
| 2002/0187560 A1* | 12/2002 | Pezzuto et al. | 436/180 |
| 2005/0106066 A1* | 5/2005 | Saltsman et al. | 422/57 |
| 2006/0062698 A1* | 3/2006 | Foster et al. | 422/101 |
| 2006/0084174 A1* | 4/2006 | Ogawa et al. | 436/63 |

OTHER PUBLICATIONS

Kim, D. S, et al., "A serpentine laminating micromixer combining splitting/recombination and advection", Lab Chip., 5(7), (Jul. 2005), 739-47.

"European Application Serial No. 14164516.8, Office Action mailed Dec. 1, 2014", 7 pgs.

"European Application Serial No. 14164516.8, Response filed Jan. 15, 2015 to Office Action mailed Dec. 1, 2014", 12 pgs.

* cited by examiner

POLYMER TEST CARTRIDGE MIXER FOR CELL LYSIS

BACKGROUND

Measuring hemoglobin in automated testing utilizes a reagent to aid in the lysis of red blood cells to release the hemoglobin into a solution from a blood sample. Simply adding a reagent to the blood sample may not be sufficient, resulting in a non-homogeneous measured sample due to incomplete lysis of cells by means of a lysing reagent.

SUMMARY

A multiple polymer layer test cartridge includes an input to receive a sample containing cells, multiple lysing channel structures on alternate layers of the multiple layer test cartridge coupled to each other to pass the sample in sequence between the lysing channel structures, and a test chamber to receive the sample from the multiple lysing channel structures.

In a further embodiment, a polymer based test cartridge includes an input to receive a sample containing red blood cells and having a reagent to mix with the sample, multiple sequential "F" shaped lysing channel structures on alternate layers of the multiple layer test cartridge coupled to each other to pass the sample in sequence between the lysing channel structures and release hemoglobin into the sample, and a test chamber to receive the sample having released hemoglobin from the multiple lysing channel structures.

A method includes receiving a blood sample, moving the blood sample through a first "F" shaped fluidic structure on a first layer of a multiple layer test cartridge, moving the blood sample from the first "F" shaped fluidic structure to a second "F" shaped fluidic structure formed on a second layer of the multiple layer test cartridge, and providing the blood sample from the first and second fluidic structures to a sampling cuvette.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Multiple fluidic structures formed in polymer layers of a test cartridge are used to mix a reagent with red blood cells. The mixing that occurs within these structures aids in the lysis of red blood cells to release hemoglobin into solution to be measured. The channel's unique shape allows for separation and recombination of sample repeatedly over a lysing reagent such that each cell is exposed to reagent and the sample is fully mixed at the point of measurement. The channels are coupled to form a chaotic advection micromixer to aid in cell lysis. The cells may be red blood cells or other cells in different embodiments, and may even work on bacteria. Some channels are also capable of lysing red blood cells without the use of a lysis reagent.

The structures may be cut from a layer of polymer material using a $CO_2$ laser. The structures are formed in at least two different layers that are laminated together to form a test cartridge. Lysing reagent is loaded in the structures and dried. Sample is loaded into the cartridge and pulled into an area of measurement at a known rate. An optical density measurement is then taken at wavelengths of 570 nm and 880 nm in one embodiment. The wavelengths of measurement and types of measurement may vary in further embodiments.

Figure 1:
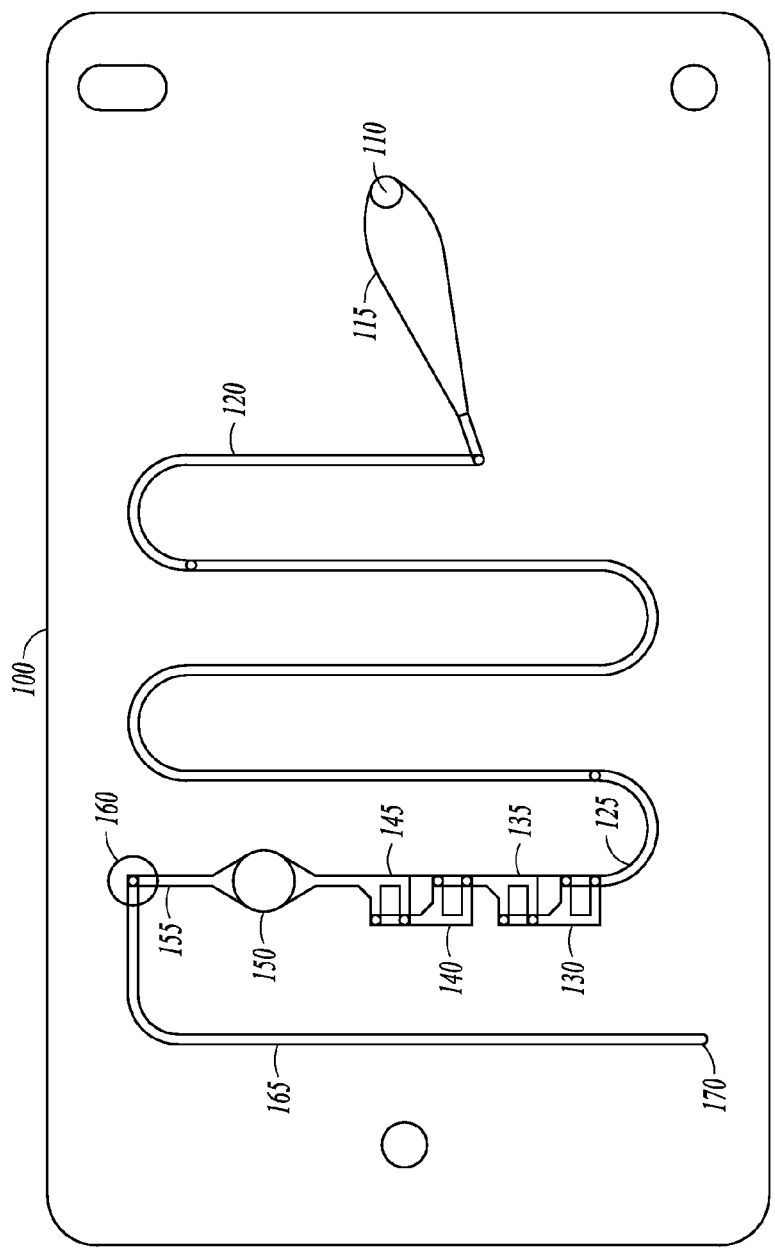
FIG. 1 is a top view of a test cartridge having sequential lysing structures according to an example embodiment.

FIG. 1 is a top view of a test cartridge 100. In some embodiments, the test card 100 contains many layers of a transparent material such as PET or other acrylic or suitable material that can be patterned with various liquid fluid transport features. The card 100 in some embodiments may be used to perform one or more blood tests utilizing a small volume of blood. The blood or other liquid to be tested, may be transported via one or more layers of the test card, and prepared for analysis by a test instrument into which the card is inserted. Various sensors, such as a combination of light emitting diodes, lasers, and photoreceptors may be used to test the liquid.

The test cartridge includes an input opening 110 where a sample enters the cartridge 100 and is held in a sample well 115. The sample is moved into a first optional channel 120, which in some embodiments is about 1 mm wide. The first channel 120 may serve to ensure that air bubbles are removed from the sample as it progresses through the first channel 120. The first channel 120 may serpentine to provide a desired length, and at an end 125 couples to a first fluidic structure 130, which is formed on a separate layer and is fluidically coupled to the end 125 of the first channel 120.

The first fluidic structure 130, also referred to as a lysing channel structure, includes a substantially straight backbone channel having a base portion and a top portion with two equal length, substantially parallel side channels extending substantially orthogonal to the top portion of the backbone channel. A second fluidic structure 135 is coupled to the first fluidic structure 130, and resides on a separate layer. The second fluidic structure may have the same shape as the first fluidic structure, with the side channels extending oppositely from the backbone, and coupled to the lower portion of the backbone of the first fluidic structure to receive the sample. The channel structures are arranged so that a channel structure receives the sample at ends of both side channels distal from its backbone. Additional fluidic structures 140, 145 are also similarly coupled to form multiple lysing channel structures on alternate layers of the multiple layer test cartridge coupled to each other to pass the sample in sequence between the lysing channel structures.

While four lysing channel structures are illustrated, as few as two, three, and more than four lysing channel structures may be used in further embodiments. Typical embodiments include 6, 7, 8, or more such structures to provide for chaotic mixing of the sample with the reagent, which may be a dried reagent provided in either or both of the first channel 120 and one or more lysing channel structures. As mentioned above, in some embodiments, a reagent is not needed to lyse some cells. If used, the reagent may be provided anywhere along the channel or in the lysing channel structures. The lysing structures cause the sample to make several 90 degree turns, both in the individual structures as the sample moves between the structures, which successively formed on different layers of the test card. Coupled structures may be formed on adjacent layers, or may even be separated by one or more layers in various embodiments that are designed to permit flow between the structures. While some structures may be formed in the same layer, alternating layers appears to provide additional chaotic mixing by forcing the sample to take more turns as it progresses through the structures.

Upon exiting the last lysing channel structure 145, the sample is sufficiently lysed, and is provided to a measuring chamber such as a cuvette 150. The cuvette 150 may further include a channel 155 leading to an optional air permeable membrane 160 that provides a stop for the sample. Other means for stopping the sample at a selected point may also be used in further embodiments. The membrane 160 sits between a layer in which the channel 155 is formed, and an exit channel 165, which exits to ambient at 170. To move the sample through the fluidic structures of the test card, either a positive or negative pressure may be applied between the end of the exit channel 165 and the sample well. In one embodiment, negative pressure is applied at 170, resulting in movement of the sample from the sample well toward the cuvette 150.

Figure 2:
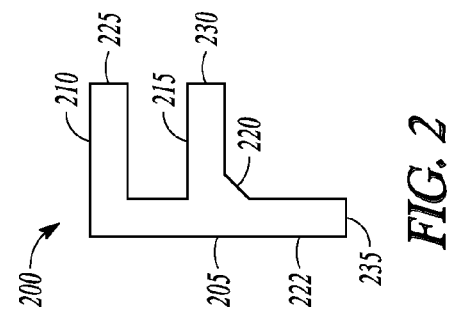
FIG. 2 is a top view of a fluidic structure to aid in lysing red blood cells.

FIG. 2 is a top view providing a larger view of an example lysing channel structure 200. Structure 200 includes a substantially straight backbone portion 205 with side channels 210 and 215 extending from the backbone portion forming a structure that is referred to as an "F" shaped structure. Structure 200 may contain a diagonal portion 220 between a bottom of side channel 215 and the side of the backbone 205 closest to a base portion 222 of the backbone. The diagonal portion 220 is adapted to reduce bubble formation as the sample moves through the channel structures. In further embodiments, the diagonal portion 220 may be curved. Side channel 210 may also include such a diagonal portion in further embodiments. In still further embodiments, the diagonal portion 220 is optional, and may not be included.

In operation, the sample is split when entering the structure 200 at ends 225, 230 of the side channels 210 and 215 distal from the backbone, and then recombined in the lower portion 222 of the backbone 205. In one embodiment, an end of the lower portion 222 is coupled to the distal end 225 of the top side channel 200 of the next lysing structure. The splitting and recombining of the sample is repeated for each successive lysing structure, as the backbone of an upstream structure is coupled to the distal ends of the succeeding lysing structure. The additional layer change between lysing structures further facilitates the chaotic mixing provided.

In further embodiments, other lysing structures may be utilized. The "F" shape may have one or more additional side channels added. An "X" shape may be used in further embodiments. Other embodiments may also utilize microfluidic chaotic mixing structures that provide for splitting, turning, and recombining the sample.

In some embodiments, the channel structures are on the order of about 1 mm in width, resulting in total sample sizes of about 5-8 μl to sufficiently lyse the sample and fill the test chamber 150 prior to encountering the membrane 160. The sizes of the channel may be varied in different embodiments to optimize performance in view of the amount of sample generally available.

Figure 3:
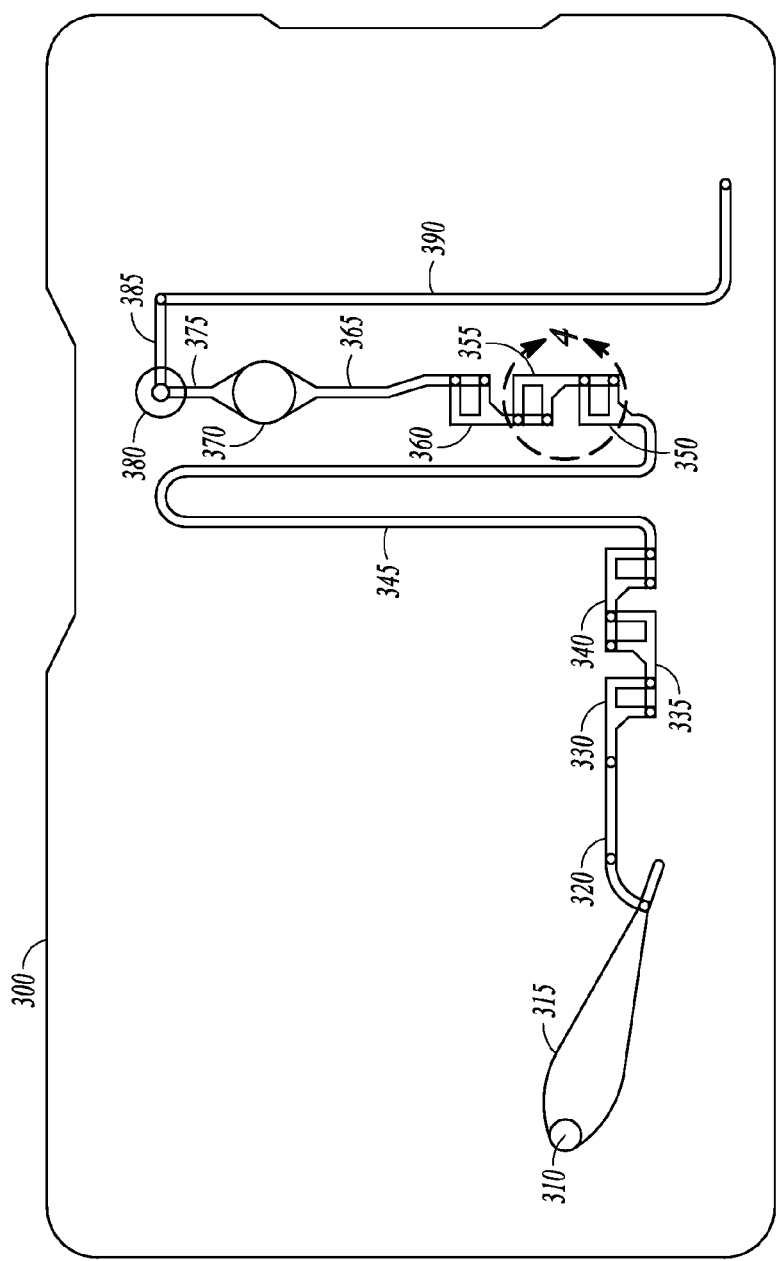
FIG. 3 is a top view of an alternative fluidic cartridge to aid in lysing red blood cells according to an example embodiment.

FIG. 3 is a top view of an alternative fluidic cartridge 300 to aid in lysing red blood cells according to an example embodiment. In some embodiments, the test card 300 contains many layers of a transparent material such as PMMA, PET, and acrylic adhesive. Once cut, they are manually assembled and pressed to seal various microfluidic features such as channels and cuvettes. The cartridge 300 in some embodiments may be used to perform one or more blood tests utilizing a small volume of blood. The blood or other liquid to be tested, may be transported via one or more layers of the test card, and prepared for analysis by a test instrument into which the card is inserted. Various sensors, such as a combination of light emitting diodes, lasers, and photoreceptors may be used to test the liquid.

The test cartridge includes an input opening 310 where a sample enters the cartridge 300 and is held in a sample well 315. The sample is moved into a first channel 320, which in some embodiments is about 1 mm wide. The first channel 320 may serve to ensure that air bubbles are removed from the sample as it progresses through the first channel 320. The first channel 320 may serpentine to provide a desired length. First channel 320 is coupled to a first fluidic structure 330, which is formed on a separate layer and is fluidically coupled to the first channel 320.

The first fluidic structure 330, also referred to as a lysing channel structure, includes a substantially straight backbone channel having a base portion and a top portion with two equal length, substantially parallel side channels extending substantially orthogonal to the top portion of the backbone channel. A second fluidic structure 335 is coupled to the first fluidic structure 330, and resides on a separate layer. The second fluidic structure may have the same shape as the first fluidic structure, with the side channels extending oppositely from the backbone, and coupled to the lower portion of the backbone of the first fluidic structure to receive the sample. The channel structures are arranged so that a channel structure receives the sample at an end of the backbone distal from the side channels, and provides the sample to the next channel structure at its backbone distal from the side channels. Additional fluidic structure 340 is also similarly coupled to form multiple lysing channel structures on alternate layers of the multiple layer test cartridge coupled to each other to pass the sample in sequence between the lysing channel structures. In one embodiment, one or more of the channels and channel structures 330, 335, 340 contain a lysing reagent that mixes with the sample. A loop 345 lengthens a reaction time between the reagent and blood resulting in a more homogeneous sample to be provided to a measurement area.

In one embodiment, three additional fluidic structures 350, 355, 360 are provided following the loop 345. One or more of these structures may also contain a lysing reagent. While six lysing channel structures are illustrated, as few as two, and more than six lysing channel structures may be used in further embodiments. Typical embodiments include 6, 7, 8, or more such structures to provide for chaotic mixing of the sample with the reagent, which may be a dried reagent provided in either or both of the first channel 320 and one or more lysing channel structures. The lysing structures cause the sample to make several 90 degree turns, both in the individual structures as the sample moves between the structures, which are successively formed on different layers of the test card. Coupled structures may be formed on adjacent layers, or may even be separated by one or more layers in various embodiments that are designed to permit flow between the structures. While some structures may be formed in the same layer, alternating layers appears to provide additional chaotic mixing by forcing the sample to take more turns as it progresses through the structures.

Upon exiting the last lysing channel structure 360, the sample is sufficiently lysed, and is provided via a channel 365 to a measuring chamber such as a cuvette 370. The cuvette 370 may further include a channel 375 leading to an optional air permeable membrane 380 that provides a stop for the sample in one embodiment. Other means of stopping the sample such that the measuring chamber contains sufficient sample may be used. The optional membrane 380 sits between a layer in which the channel 375 is formed, and an exit channel 385, which exits to ambient at 390. To move the sample through the fluidic structures of the test card, either a positive or negative pressure may be applied between the end of the exit channel 375 and the sample well 370. In one embodiment, negative pressure is applied at 390, resulting in movement of the sample from the sample well toward the membrane 380.

Figure 4:
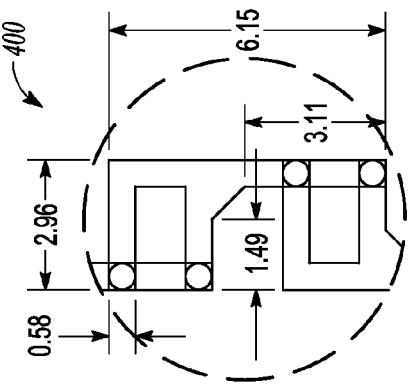
FIG. 4 is a top view of an example lysing structure with example dimensions according to an example embodiment.

FIG. 4 is a top view of an example lysing "F" shaped structure 400 with example dimensions in µm according to an example embodiment.

Figure 5:
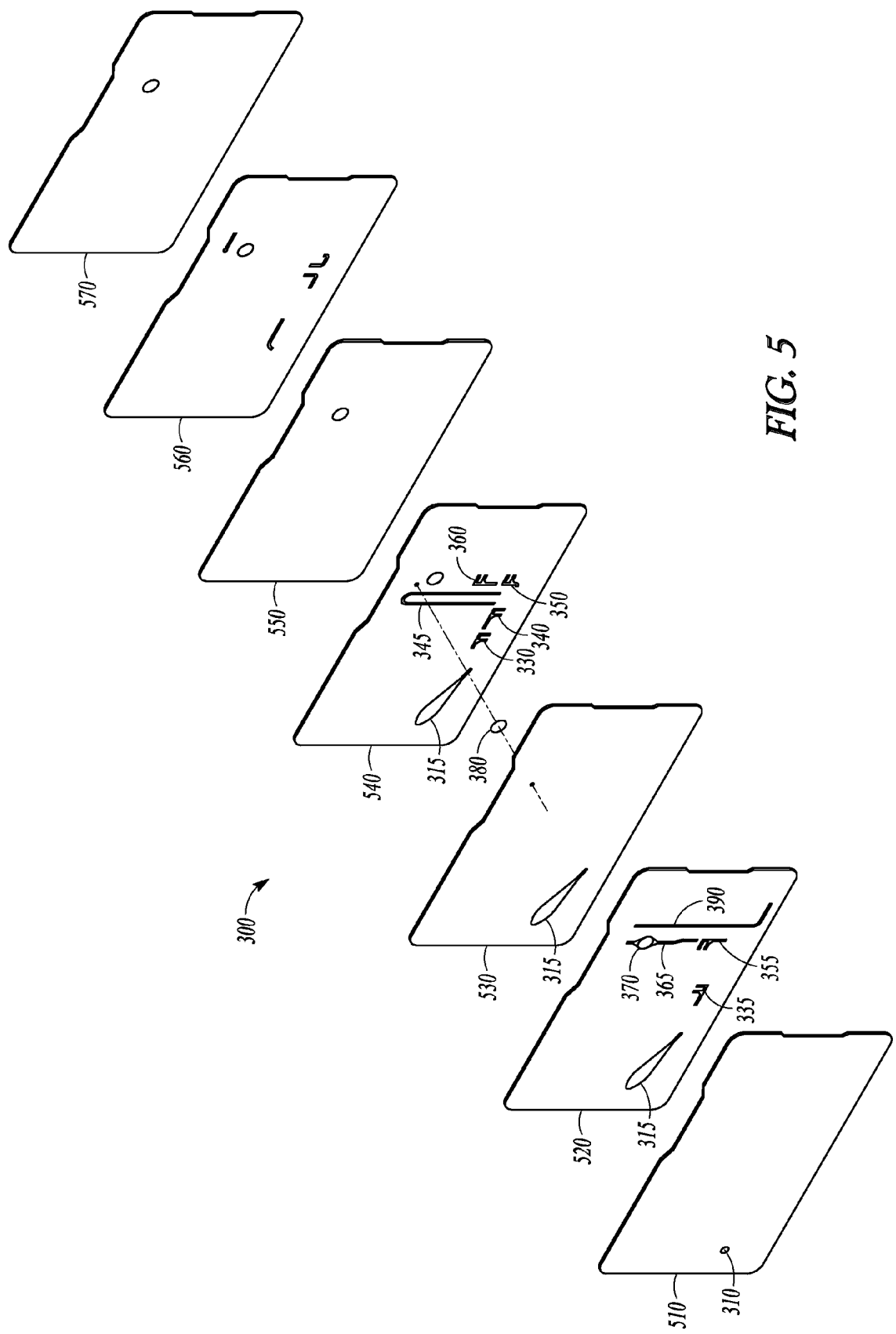
FIG. 5 is an exploded view of the cartridge of FIG. 3 illustrating individual layers according to an example embodiment.

FIG. 5 is an exploded view of the cartridge 300 of FIG. 3 illustrating individual layers 510, 520, 530, 540, 550, 560, and 570 according to an example embodiment. Features formed in the layers are identified with the same reference numbers as used in FIG. 3.

EXAMPLES

1. A test cartridge comprising:
an input to receive a sample containing cells;
multiple lysing channel structures on alternate polymer layers of the multiple layer test cartridge coupled to each other to pass the sample in sequence between the lysing channel structures; and
a test chamber to receive the sample from the multiple lysing channel structures.

2. The test cartridge of example 1 wherein the lysing channel structures have a letter "F" shape.

3. The test cartridge of example 2 wherein the lysing channel structure comprises a substantially straight backbone channel having a base portion and a top portion with two equal length, substantially parallel side channels extending substantially orthogonal to the top portion of the backbone channel.

4. The test cartridge of example 3 wherein the channel structures are arranged so that a first lysing channel structure receives the sample at ends of both side channels distal from its backbone.

5. The test cartridge of example 4 wherein a second lysing channel structure is positioned on a different layer from the first lysing channel structure and has ends of both side channels coupled to receive sample from the base portion of the backbone of the first channel structure.

6. The test cartridge of example 5 and further comprising multiple additional sequential lysing channel structures each having the same shape and connection to a preceding channel structure.

7. The test cartridge of example 6 wherein at least two channel structures are separated by a loop channel configured to facilitate mixing of a reagent with the fluid.

8. The test cartridge of example 5 wherein the lysing channel structure has a diagonal portion between a bottom of the side channel and the backbone closest to the base portion of the backbone.

9. The test cartridge of example 8 wherein the diagonal portion is adapted to reduce bubble formation as sample moves through the channel structures.

10. The test cartridge of any of examples 1-9 and further comprising an exit channel coupled to ambient on a different polymer layer than the test chamber.

11. The test cartridge of any of examples 1-10 and further comprising a reagent positioned in at least one of the input and selected lysing channels.

12. The test cartridge of any of examples 1-11 wherein the alternate layers are adjacent layers.

13. The test cartridge of any of examples 1-12 wherein at least some alternate layers are separated by at least one layer.

14. A multiple layer test cartridge comprising:
an input to receive a sample containing red blood cells and having a reagent to mix with the sample;
multiple sequential "F" shaped lysing channel structures on alternate layers of the multiple layer test cartridge laminated to each other to pass the sample in sequence between the lysing channel structures and release hemoglobin into the sample; and
a test chamber to receive the sample having released hemoglobin from the multiple lysing channel structures.

15. The test cartridge of example 14 wherein the channel structure comprises a substantially straight backbone channel having a base portion and a top portion with two equal length, substantially parallel side channels extending substantially orthogonal to the top portion of the backbone channel.

16. The test cartridge of example 15 wherein the channel structures are arranged so that a first channel structure receives the sample at ends of both side channels distal from its backbone, wherein a second channel structure is positioned on a different layer from the first channel structure and has ends of both side channels coupled to receive sample from the base portion of the backbone of the first channel structure.

17. A method comprising:
receiving a blood sample;
moving the blood sample through a first "F" shaped fluidic structure on a first polymer layer of a multiple laminated layer test cartridge;
moving the blood sample from the first "F" shaped fluidic structure to a second "F" shaped fluidic structure formed on a second layer of the multiple layer test cartridge; and
providing the blood sample from the first and second fluidic structures to a sampling cuvette.

18. The method of example 17 and further comprising moving the blood sample through multiple additional sequentially disposed "F" shaped fluidic structures on different layers of the test cartridge.

19. The method of any of examples 17-18 and further comprising adding a reagent to the blood sample prior to moving the blood samples through the "F" shaped fluidic structures.

20. The method of example 19 wherein the reagent is added to the blood sample in one of the "F" shaped fluidic structures and mixed with the blood sample by a loop channel positioned between two of the "F" shaped fluidic structures.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A multiple layer test cartridge comprising:
   an input opening to receive a sample containing cells;
   an input channel coupled to the input opening to receive the sample from the input opening;
   a first lysing channel structure coupled to the input channel and adapted to receive the sample from the input channel, the first lysing channel structure having two side channels coupled to and extending away from an input channel and adapted such that the sample in the input channel is split between the two side channels, the first lysing channel structure having a backbone channel orthogonally coupled to the two side channels and adapted to receive and recombine the split sample;
   a second lysing channel structure having two side channels coupled to and extending away from the backbone channel of the first lysing channel structure and adapted such that the sample in the backbone of the first lysing channel structure is split between the two side channels of the second lysing channel structure, the second lysing channel structure having a backbone channel orthogonally coupled to the two side channels of the second lysing channel structure and adapted to receive and recombine the split sample;
   wherein the first lysing channel structure is disposed in a first polymer layer of the multiple layer test cartridge and the second lysing channel structure is disposed in a second polymer layer of the multiple layer test cartridge different from the first polymer layer, wherein the first and second lysing channel structures are adapted to lyse the cells in the sample; and
   a test chamber coupled to the backbone channel of the second lysing channel structure and is adapted to receive the recombined sample from the backbone channel of the second lysing channel structure.

2. The test cartridge of claim wherein each lysing channel structure has a letter "F" shape comprising the backbone channel being a straight channel having a base portion and a top portion including the two side channels being two equal length parallel side channels extending orthogonally to the top portion of the backbone channel.

3. The test cartridge of claim 1, wherein the second lysing channel structure is positioned on a different polymer layer from the first lysing channel structure and has ends of both side channels coupled to the base portion of the backbone channel to receive sample from a base portion of the backbone channel of the first lysing channel structure.

4. The test cartridge of claim 3, further comprising at least two additional lysing channel structures each having the same shape as the first and second lysing channel structures, and each coupled to a backbone channel of a preceding lysing channel structure, wherein the at least two additional lysing channel structures are coupled in series between the first and second lysing channel structures to create a series of four lysing channel structures between the input channel and the test chamber, wherein each lysing channel structure in the series is in a different polymer layer from a preceding lysing channel structure to provide microfluidic mixing structures that provide for repeated splitting, turning and recombining of the sample as it progresses through the series of four lysing channel structures.

5. The test cartridge of claim 4, further comprising a loop channel fluidically coupled between two of the coupled lysing channel structures in the series to facilitate mixing of a reagent with the sample.

6. The test cartridge of claim 3, further comprising a diagonal portion fluidically coupled between a bottom of the side channel closest to the base portion of the backbone channel and the backbone channel of at least one of the first and second lysing channel structures.

7. The test cartridge of claim 1, further comprising an exit channel fluidically coupled between the test chamber and the backbone channel of the second lysing channel structure.

8. The test cartridge of claim 1, further comprising a reagent positioned in at least one of the input channel and the lysing channel structures.

9. The test cartridge of claim 1, wherein the first and second polymer layers are adjacent layers.

10. The test cartridge of claim 1, further comprising at least one polymer layer located between the first and second polymer layers.

11. A multiple layer test cartridge comprising:
    an input opening to receive a sample containing red blood cells;
    an input channel coupled to the input opening and adapted to receive the sample from the input opening;
    a sequence of multiple fluidically coupled lysing channel structures, wherein each of the lysing channel structures comprise a backbone channel and two side channels orthogonally connected to the backbone channel;
    wherein a first lysing channel structure in the sequence of lysing channel structures is fluidically coupled to the input channel and adapted to receive the sample from the input channel via the two side channels;
    wherein each of the lysing channel structures fluidically connected to and after the first lysing channel structure in the multiple lysing channel structure sequence have the side channels coupled orthogonally to the backbone channel of a preceding lysing channel structure;
    a plurality of adjacent layers;
    wherein the lysing channel structures are each disposed in a layer and each of the lysing channel structures are alternately disposed in different layers and adapted to pass the sample in the sequence of lysing channel structures between the lysing channel structures to provide microfluidic mixing structures that provide for repeated splitting, turning and recombining of the sample; and
    a test chamber coupled to the multiple lysing channel structures in the sequence and adapted to receive the sample from the multiple lysing channel structures.

12. The test cartridge of claim 11 wherein, each lysing channel structure comprises the backbone channel being a substantially straight channel having a base portion and a top portion including the two side channels being two equal length, substantially parallel side channels extending substantially orthogonal to the top portion of the backbone channel.

13. The test cartridge of claim 12 wherein, the lysing channel structures are arranged no that the first lysing channel structure receives the sample at and end of both side channels distal from the first lysing channel backbone channel, wherein a next lysing channel structure in the sequence of lysing channel structures is positioned on a different polymer layer from the first lysing channel structure and has and end of both side channels coupled to receive sample from the base portion of the backbone channel of the first lysing channel structure.

* * * * *